United States Patent [19]

Hiestand et al.

[11] 4,165,435

[45] Aug. 21, 1979

[54] FIRE RETARDANT S-TRIAZINE DERIVATIVES

[75] Inventors: Armin Hiestand, Binningen; Peter Rohringer, Schönenbuch, both of Switzerland

[73] Assignee: Ciba-Geigy Corporation, Ardsley, N.Y.

[21] Appl. No.: 808,009

[22] Filed: Jun. 20, 1977

[30] Foreign Application Priority Data

Jun. 25, 1976 [CH] Switzerland .................. 8156/76

[51] Int. Cl.$^2$ ................. C07D 251/38; C07D 251/52; C07D 251/66
[52] U.S. Cl. ................. 544/197; 544/199; 544/208; 544/210; 544/211; 544/213; 544/219
[58] Field of Search ............... 544/197, 199, 208, 210, 544/211, 213, 219

[56] References Cited

U.S. PATENT DOCUMENTS

| | | | |
|---|---|---|---|
| 2,312,698 | 3/1943 | D'Alelio | 544/197 |
| 3,054,792 | 9/1962 | Howard et al. | 544/211 |
| 3,210,339 | 10/1965 | Schwarze | 544/210 |
| 3,783,017 | 1/1974 | Roth | 117/136 |

FOREIGN PATENT DOCUMENTS

1694220  7/1971  Fed. Rep. of Germany .

*Primary Examiner*—Alan L. Rotman
*Assistant Examiner*—Jane T. Fan

*Attorney, Agent, or Firm*—Prabodh I. Almaula

[57] ABSTRACT

A s-Triazine of the formula wherein X, Y and Z are radicals of the formula $$-(NR)_{n-1}-SO_2-N\begin{matrix}R\\R\end{matrix} \quad \text{or} \quad -N\begin{matrix}\text{(benzisothiazole-1,1-dioxide)}\end{matrix}$$

and R are aromatic, cycloaliphatic or aliphatic radicals or hydrogen is provided.

The process for the manufacture of such s-Triazines is also provided as well as a process for fireproofing polyester fibres with such s-Triazines. The s-Triazine may also be applied in the presence of a dispersant, a protective colloid and/or water. The composition of matter for performing this process is also provided.

2 Claims, No Drawings

FIRE RETARDANT S-TRIAZINE DERIVATIVES

The invention relates to an s-triazine of the formula

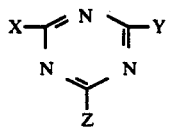
(1)

wherein X represents a radical of the formula

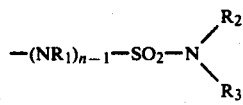
(1.1)

wherein n represents 1 or 2, $R_1$ represents phenyl optionally substituted by methyl, ethyl, sulphonamido or carboxylamido, or hydrogen, $R_2$ and $R_3$ each have the meanings given for $R_1$ or represent benzyl, phenylethyl, cyclohexyl, or alkyl which has 1 to 4 carbon atoms and which is optionally substituted by hydroxyl, methoxy or ethoxy, or $R_2$ and $R_3$ together represent alkylene having 4 to 5 carbon atoms or ethyleneoxyethylene, or X represents a radical of the formula

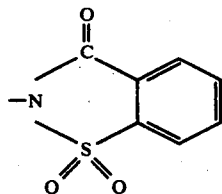
(1.2)

and Y and Z each have the meanings given for X or represent alkylamino or dialkylamino having 1 to 4 carbon atoms per alkyl radical, and, where n in the formula (1.1) represents 2, Y and Z also represent alkoxy having 1 to 8 carbon atoms, phenoxy alkylphenoxy having 1 to 4 carbon atoms in the alkyl radical, benzyloxy, halogen or hydroxyl.

Preferred reaction products correspond to the formula (1) wherein X and Y each represent a radical of the formulae (1.1) and (1.2), and preferably the same radical of one of the formulae (1.1) or (1.2), and Z has the meanings given for X and Y.

In particular, the preferred s-triazines correspond to the formula

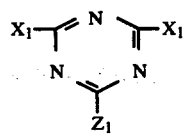
(2)

wherein $X_1$ represents a radical of the formula

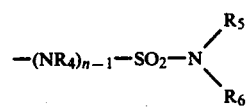
(2.1)

wherein n represents 1 or 2, $R_4$ represents phenyl or hydrogen, $R_5$ and $R_6$ each have the meanings given for $R_4$, or represent benzyl, phenylethyl, cyclohexyl, alkyl having 1 to 4 carbon atoms, or $R_5$ and $R_6$ together represent alkylene having 4 to 5 carbon atoms, or $X_1$ represents a radical of the formula (1.2), and $Z_1$ has the meanings given for $X_1$, or represents alkylamino or dialkylamino having 1 to 4 carbon atoms per alkyl group, and, where n in formula (2.1) represents 2, $Z_1$ represents alkoxy having 1 to 4 carbon atoms, phenoxy, benzyloxy, chlorine or hydroxyl.

Of particular interest are s-triazines of the formula

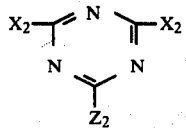
(3)

wherein $X_2$ represents a radical of the formula

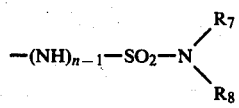
(3.1)

wherein n represents 1 or 2, and $R_7$ and $R_8$ each represent phenyl, benzyl, alkyl having 1 to 4 carbon atoms, or hydrogen, or $X_2$ represents a radical of the formula (1.2), and $Z_2$ has the meanings given for $X_2$, or represents diethylamino or dimethylamino, and, where n in formula (3.1) represents 2, $Z_2$ also represents ethoxy, methoxy, phenoxy or benzyloxy.

Of primary interest are s-triazines of the formula

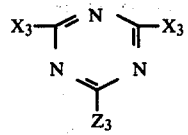
(4)

wherein $X_3$ represents a radical of the formula

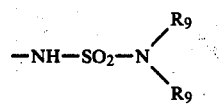
(4.1)

wherein $R_9$ represents methyl or hydrogen, or $X_3$ represents a radical of the formula (1.2), and $Z_3$ has the meanings given for $X_3$ or represents methoxy, phenoxy or benzyloxy.

In the definitions of the R radicals and Z radicals, alkyl radicals are, e.g., n-butyl, sec.-butyl, isobutyl, n-propyl, isopropyl, ethyl or methyl. In the definition of Z, alkoxy can denote radicals such as n-octoxy, n-heptoxy or n-hexoxy, and especially, e.g., n-butoxy, tert.-butoxy, isobutoxy, n-propoxy, isopropoxy, ethoxy or particularly methoxy. If $R_2$ and $R_3$ together represent alkylene, they form together with the nitrogen atom to which they are bound a hetero ring, e.g. a piperidine ring or pyrrolidine ring, and in the case where $R_2$ and $R_3$ together represent ethylene-oxyethylene, they form with the nitrogen atom a morpholine radical.

The radical of the formula (1.2) is derived from saccharin.

The following compounds in Table I may be given as examples of specific s-triazines of the formula (1).

TABLE I

| No. | X | Y | Z |
|---|---|---|---|
| 1 | *benzisothiazolone-dioxide-N-CH2 group* | *benzisothiazolone-dioxide-N-CH2 group* | CH3O— |
| 2 | *benzisothiazolone-dioxide-N-CH2 group* | *benzisothiazolone-dioxide-N-CH2 group* | *benzisothiazolone-dioxide-N-CH2 group* |
| 3 | (H3C)2N—SO2—NH— | (H3C)2N—SO2—NH— | (H3C)2N—SO2—NH— |
| 4 | (H3C)2N—SO2— | (H3C)2N—SO2— | (H3C)2N—SO2— |
| 5 | H2N—SO2—NH— | H2N—SO2—NH— | H2N—SO2—NH— |
| 6 | C6H5—NH—SO2— | C6H5—NH—SO2— | C6H5—NH—SO2— |
| 7 | n-C4H9—NH—SO2— | n-C4H9—NH—SO2— | n-C4H9—NH—SO2— |
| 8 | (H3C)2N—SO2— | (H3C)2N—SO2— | (H5C2)2N— |
| 9 | (H3C)2N—SO2— | (H3C)2N—SO2— | (H3C)2CH—NH— |
| 10 | H2N—SO2— | H2N—SO2— | H2N—SO2— |
| 11 | H3C—NH—SO2— | H3C—NH—SO2— | H3C—NH—SO2— |
| 12 | H2N—SO2—NH— | H2N—SO2—NH— | CH3O— |
| 13 | H2N—SO2—NH | H2N—SO2—NH— | C6H5—O— |
| 14 | H2N—SO2—NH— | H2N—SO2—NH— | C6H5—CH2—O— |
| 15 | *benzisothiazolone-dioxide-N-CH2 group* | *benzisothiazolone-dioxide-N-CH2 group* | C6H5—O— |
| 16 | *benzisothiazolone-dioxide-N-CH2 group* | *benzisothiazolone-dioxide-N-CH2 group* | C6H5—CH2—O— |

Of particular practical importance are the compounds Nos. 1 to 4 of Table I.

The present invention relates also to a process for producing the novel s-triazines of the formula (1), which process comprises reacting the compound of the formula

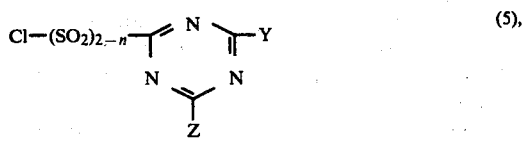

(5), wherein Y and Z have the given meanings, with a compound of the formula

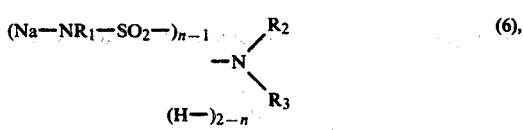

(6), wherein $R_1$, $R_2$ and $R_3$ have the given meanings, and n in the formulae (1.1), (5) and (6) has the same meaning 1 or 2; or, if n represents 2, with the compound of the formula

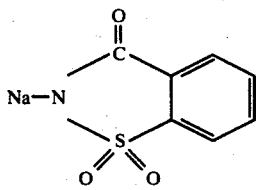

In particular, the compound of the formula (2) is produced by reacting 1 mole of the compound of the formula

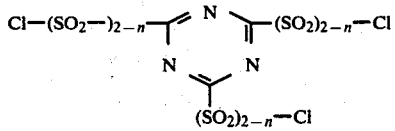

with 3 moles of the compound of the formula

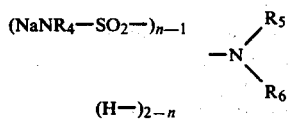

wherein $R_4$, $R_5$ and $R_6$ have the given meanings, and n in the formulae (2.1), (8) and (9) has the same meaning 1 or 2; or, if n represents 2, with 3 moles of the compound of the formula (7); or by reacting 1 mole of the compound of the formula

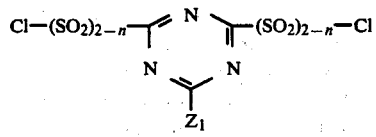

wherein $Z_1$ and n have the given meanings, with 2 moles of the compound of the formula (9); or, if n in the formula (10) represents 2, with 2 moles of the compound of the formula (7).

The compound of the formula (3), which is of special interest, is produced by reacting 1 mole of the compound of the formula (8) with 3 moles of the compound of the formula

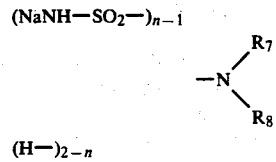

wherein $R_7$ and $R_8$ have the given meanings, and n in the formulae (3.1), (8) and (11) has the same meaning 1 or 2; or, if n represents 2, with 3 moles of the compound of the formula (7); or by reacting 1 mole of the compound of the formula

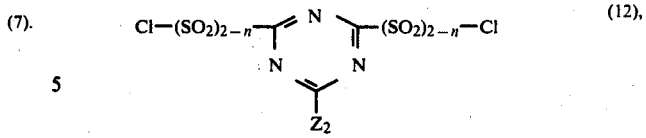

wherein n and $Z_2$ have the given meanings, with 2 moles of the compound of the formula (11); or, if n in formula (12) represents 2, with 2 moles of the compound of the formula (7).

The compound of the formula (4), which is of primary interest, is produced by reacting 1 mole of cyanuric chloride with 3 moles of the compound of one of the formulae $$H_2N-SO_2-NH-Na \qquad (13),$$

$$(CH_3)_2-N-SO_2-NH.Na \qquad (14)$$

or (7), or by reacting 1 mole of the compound of the formula

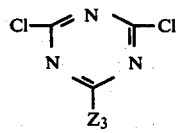

wherein $Z_3$ has the given meanings, with 2 moles of the compound of one of the formulae (13), (14) or (7).

The starting compounds (5), (8), (10), (12) and (15) are known. The di- and tri-sulphochlorides, i.e. the compounds of the formulae (5), (8), (10) and (12) wherein n represents 1, are obtained by chlorination with chlorine gas of the corresponding di- and trimercapto-s-triazines in acetic acid/aqueous medium at 0° to 5° C.

The reaction of the s-triazine-2,4,6-trisulphochlorides and the s-triazine-4,6-disulphochlorides, i.e. the compounds (5), (8), (10) and (12) wherein n represents 1, is performed with the amines of the formulae (6), (9) and (11) wherein n represents 1, in an aqueous medium at 20° to 80° C., preferably at 50° to 60° C.

The reaction of cyanuric chloride or of 4,6-dichloro-s-triazines, i.e. of the starting compounds of the formulae (5), (8), (10) and (12) wherein n represents 2, or of the starting compound of the formula (15), is performed with the sulphurylamide sodium compounds of the formulae (6), (9) and (11) wherein n represents 2, with the sulphurylamide sodium compounds of the formulae (13) and (14), or with the sodium saccharinate of the formula (7), in an inert organic solvent, e.g. in acetone and ethanol, at 20° to 80° C., preferably at the reflux temperature of the employed solvent, e.g. at 55° to 80° C.

The resulting s-triazines according to the invention are processed by customary methods which are described in the following Examples 1 to 16.

The s-triazines according to the invention are in particular effective fireproofing agents for the fireproofing of fiber materials made from polyester. Hence the present invention relates further to the use of the s-triazines according to the invention as flameproofing agents, to the application process by which these s-triazines are used to fireproof the fiber materials, to the composition for carrying out the application process, which composition contains the s-triazines according to the invention, and to the fiber material to which has been imparted the flameproof finish by means of the application process. The process according to the invention for fireproofing fiber materials made from polyester is characterised in that these materials are treated with a preparation which contains at least one s-triazine of the formula (1); and the materials treated in this manner are subjected to a heat treatment.

The s-triazines of the formula (1) are solid compounds which are soluble or insoluble in water. Products soluble in water are applied to the fiber materials from aqueous solutions; products insoluble in water are applied to the fiber materials from aqueous dispersions. Products insoluble in water can also be applied from an organic solution.

With the application of water-insoluble s-triazines of the formula (1) from an aqueous suspension or dispersion, there are preferably used dispersing agents of the type customarily used in the dyestuff and textile industries, e.g. lignin sulphonates, aromatic sulphonic acids, saturated-aliphatic dicarboxylic acids substituted with higher alkyl radicals, condensation products from aromatic sulphonic acids and formaldehyde, alkylphenol-/ethylene oxide adducts, ethylene oxide adducts from fatty acids, fatty amines or fatty alcohols, sulphurated substituted benzimidazoles and sulphonated fatty acid amides. Good results are obtained in particular with lignin sulphonates, with ethylene oxide adducts from alkylphenols, fatty amines, fatty alcohols or fatty acids, and especially with substituted benzimidazoles or with condensation products from aromatic sulphonic acids with formaldehyde.

There are preferably employed those dispersing agents which at elevated temperature, e.g. at 180° C. to 220° C., cause no yellowing of the treated substrate, or at most a yellowing that is removed by subsequent washing. In other words, the dispersing agents either should not decompose at elevated temperature or should merely form soluble or volatile decomposition products. The amount of dispersing agent used is preferably between 1 and 60 percent by weight, relative to the s-triazine. Particularly good results are obtained with 1 to 50, especially with 1 to 20, and particularly with 1 to 4 percent by weight of dispersing agent, relative to the s-triazine.

In order to increase storage stability, the aqueous suspensions or dispersions can also contain a protective colloid. The protective colloids customarily employed in industry are suitable, such as polyvinyl alcohol, polyvinylpyrrolidone, methylcellulose, carboxymethylcellulose, hydroxyethylcellulose or hydroxypropylcellulose, gelatine, acid casein, starch paste, or polymers of monomers of the acrylic acid series, such as polyacrylic acid, ethyl acrylate copolymers or methyl methacrylate copolymers. Good results are obtained in particular with polyvinyl alcohol, hydroxyethylcellulose and especially with carboxymethylcellulose.

The aqueous preparations contain as a rule 50 to 700 g/kg, preferably 200 to 700 g/kg, particularly 200 to 500 g/kg, of s-triazine; 0 to 300 g/kg, preferably 0.2 to 200 g/kg, especially 5 to 40 g/kg, of dispersing agent; and 0 to 30 g/kg or 0.5 to 30 g/kg, preferably 0 to 10 or 0.5 to 10 g/kg of protective colloid. The amount is made up each time with water to 1 kg.

The s-triazine of the formula (1) is advantageously ground as an aqueous dispersion in the presence of a dispersing agent to the extent that the particles have a mean diameter of 0.5 to 30$\mu$, preferably 0.5 to 20$\mu$. Good results are obtained in particular with dispersions of which the particle size is 0.5 to 10$\mu$, especially 0.5 to 5$\mu$. The particle size in itself has no influence on the attainable fireproofing effects, but does influence the stability of the dispersions.

The s-triazines of the formula (1) wet in different ways, so that it can be advantageous to suspend them in water not immediately before application but already well beforehand. Pure suspensions are however relatively unstable. There is therefore preferably added to the aqueous preparation a dispersing agent, since this prevents a rapid sedimentation of the solid s-triazine. This sedimentation can be almost completely prevented by the further addition of a protective colloid. The protective colloids can be incorporated into the dispersion before or after grinding. Dispersions thus stabilised can if required be converted by drying in a manner known per se, e.g. in a spray dryer or in a customary paddle dryer, into solid commercial preparations which can be redispersed an any time.

The grinding of the solid s-triazines is performed in standard equipment suitable for the purpose, e.g. in a glass-ball mill, in a sand mill or in a corundum disk mill.

Suitable organic solvents for application of the s-triazines of the formula (1) from an organic solution are aromatic hydrocarbons, e.g. benzene or toluene, particularly cycloaliphatic or heterocyclic hydrocarbons, e.g. dioxane or tetrahydrofuran, halogenated, preferably aliphatic, hydrocarbons, e.g. chloroform or trichloroethylene, and especially lower, preferably aliphatic, alcohols, e.g. methanol or ethanol, ketones, e.g. cyclohexanone, acetone or methyl ethyl ketone, esters, e.g. ethyl acetate or amides, e.g. dimethylformamide.

The process according to the invention is preferably performed by drying the fiber material after it has been treated with the aqueous fireproofing composition and subsequently subjecting the dried material to a heat treatment at elevated temperature. One suitable method comprises drying the treated material at temperatures up to 100° C., e.g. at 70° to 100° C., and then subjecting it to a heat treatment above 100° C., e.g. at 100° to 220° C., or especially at 150° to 220° C., i.e. subjecting it to a thermosol treatment.

The fireproofing composition containing the s-triazine of the formula (1) can be applied to the fiber materials by conventional methods, e.g. by spraying or printing, or preferably by the exhaust process, or particularly by padding.

The thermosol process is preferably performed, after padding, at 175° C. to 220° C., and requires as a rule 10 to 200 seconds, preferably 20 to 100 seconds. Particularly good results are achieved with a time of 10 to 60 seconds.

Alternatively, the materials may also be finished by the exhaust process under high-temperature conditions, e.g. at 100° C. to 130° C.

The process according to the invention is performed preferably in such a manner that, by suitable dilution of the fireproofing composition with water or with organic solvent, depending on the type of fiber material and on its weight per unit area, the deposit of s-triazine of the formula (1), relative to the fiber material treated, is 1 to 20 percent by weight or, in particular, 1 to 10 percent by weight.

The polyester fiber materials rendered fireproof according to the invention can be any stage of processing, i.e. they can be treated in the form of staple or continuous filaments, in the form of fabrics or knitwear, in the dyed or undyed condition, or in the form of textiles which have already been further processed. Preferably however the material to be treated is always textile fiber material.

Preferably, the fireproof finish is imparted to polyester fiber materials, which are derived in particular from terephthalic acid, e.g. poly(ethylene glycol terephthalate).

There are obtained according to the invention on polyester fiber materials permanent fireproofing effects, which are retained even after repeated washing or dry cleaning. The finishes have the additional advantage that the handle of the fireproofed fiber materials is not found to be tacky. Moreover, the tendency of the fabrics to become soiled in the dry state and in the wet state is not increased. The fastness to light and rubbing of the dyeings is scarcely affected.

A particular advantage of the process according to the invention for the fireproofing of polyester fiber materials is that good fireproofing effects are obtained with small deposited amounts.

The textile-mechanical properties of the treated fiber materials are moreover not disadvantageously affected by the present fireproofing finish, and the good handle properties of the treated fabrics are scarcely impaired. The same applies to the low stiffness in flexure and to the high ultimate tensile strength of the fireproofed fiber materials. Even fabrics treated with disperse dyes can be treated according to the invention without the quality of the printing suffering.

The process according to the invention for the fireproofing of polyester fiber materials can be performed also simultaneously with a process for dyeing or brightening.

Percentage values in the following Examples are percent by weight, and 'parts' are parts by weight.

EXAMPLE 1

18 parts (0.1 mole) of 2-methoxy-4,6-dichloro-s-triazine, dissolved in 400 parts of acetone are reacted with 48 parts (0.2 mole) of the compound of the formula (7), which is present as dihydrate, for 8 hours at the reflux temperature of 55° to 58° C. After separation of the sodium chloride, formed by the reaction, from the reaction mixture, the compound No. 1 according to Table 1 is isolated, from the acetonic solution, as a crystalline substance.

Elementary analysis: Calculated: C, 45.67%; N, 14.79%; S, 13.54%; H, 2.34%; O, 23.66%. Found: C, 45.1%; N, 15.0%; S, 13.1%; H, 2.3%; 0, 23.5%.

EXAMPLE 2

18.4 parts (0.1 mole) of cyanuric chloride dissolved in 400 parts of acetone and 72.5 parts (0.3 mole) of the compound of the formula (7) are reacted with each other as given in Example 1 and then processed.

The compound No. 2 according to Table 1 is obtained as a pulverulent substance.

Elementary analysis: Calculated: C, 46.15%; N, 13.46%; S, 15.40%; H, 1.94%; O, 23.05%. Found: C, 45.5%; N, 13.8%; S, 14.9%; H, 2.0%; O, 23.8%.

EXAMPLE 3

24.7 parts (0.134 mole) of cyanuric chloride dissolved in 160 parts of acetone and 59 parts (0.4 mole) of the compound of the formula (14) dissolved in 160 parts of ethanol are reacted with each other for 18 hours at the reflux temperature of 55° to 58° C. After removal of the acetone by distillation, the ethanolic reaction mixture, now present as dispersion, is heated at 78° to 81° C. for a further 6 hours and then filtered hot. After distilling off the ethanolic yellow solution, there is obtained the compound No. 3 according to Table I in the form of a crystalline substance.

Elementary analysis: Calculated: C, 24.16%; N, 28.17%; S, 21.49%; H, 4.73%; O, 21.45%. Found: C, 23.8%; N, 28.4%; S, 21.8%; H, 4.6%; O, 21.4%.

EXAMPLE 4

53.2 parts (0.3 mole) of 2,4,6-trimercapto-s-triazine are dispersed in 200 parts of water and 200 parts of glacial acetic acid. Into the trimercaptotriazine dispersion is introduced chlorine gas, in a finely dispersed form, at 5° C. for 2½ hours. The s-triazine-2,4,6-trisulphochloride thus obtained is filtered off, washed with water at 1° to 3° C. and immediately redispersed in 100 parts of water at 1° to 3° C. To this dispersion is now added, within 30 minutes, 208 parts of a 40% aqueous dimethylamine solution (1.84 moles). The reaction mixture is heated to 50° to 55° C. and kept at this temperature for 2 hours. The reaction mixture, darkly coloured, is concentrated to ⅓ of its volume, allowed to stand for 15 hours and filtered. The filtered-off reaction product is dispersed in 200 parts of water, the dispersion is adjusted to pH 4 with glacial acetic acid and filtered. The filtered-off product is recrystallised from ethanol to obtain the compound No. 4 according to Table I in the form of a crystalline substance.

Elementary analysis: Calculated: C, 26.86%; N, 20.88%; S, 23.90%; H, 4.51%; O, 23.85%. Found: C, 27.0%; N, 20.8%; S, 23.3%; H, 4.3%; O, 24.6%.

EXAMPLE 5

24.7 parts (0.134 mole) of cyanuric chloride, dissolved in 200 parts of acetone, and 47.2 parts (0.4 mole) of the compound (13), dispersed in 200 parts of acetone, are reacted as described in Example 1. After distilling off the acetone from the filtered solution, there is obtained the compound No. 5 according to Table I in the form of a pulverulent substance.

Elementary analysis: Calculated: C, 9.92%; N, 34.69%; S, 26.47%; H, 2.50%; O, 26.42%. Found: C, 10.4%; N, 33.9%; S, 26.0%; H, 2.6%; O, 27.1%.

EXAMPLE 6

The procedure is carried out as given in Example 4 except that to the aqueous s-triazine-2,4,6-trisulphochloride dispersion at 1° to 3° C. are added 186 parts (2 moles) of aniline in place of 208 parts of the 40% aqueous dimethylamine solution. The compound No. 6 according to Table I is obtained as a crystalline substance.

Elementary analysis: Calculated: C, 46.15%; N, 15.38%; S, 17.60%; H, 3.32%; O, 17.55%. Found: C, 45.6%; N, 15.3%; S, 16.9%; H, 3.6%; O, 18.6%.

EXAMPLE 7

The process is carried out as given in Example 4 except that to the aqueous s-triazine-1,3,5-trisulphochloride dispersion at 1° to 3° C. are added 146 parts (2 moles) of n-butylamine in place of 208 parts of the 40% aqueous dimethylamine solution. The compound No. 7 according to Table I is obtained as a crystalline substance.

Elementary analysis: Calculated: C, 37.02%; N, 17.27%; S, 19.76%; H, 6.21%; O, 19.74%. Found: C, 36.9%; N, 17.8%; S, 19.6%; H, 6.1%; O, 19.6%.

EXAMPLE 8

The procedure is carried out as given in Example 4 except that 129.6 parts (0.6 mole) of 2-diethylamino-4,6-dimercapto-s-triazine are introduced instead of 53.2 parts (0.3 mole) of 2,4,6-trimercapto-s-triazine, and to the resulting aqueous s-triazine-2-diethylamido-4,6-disulphochloride dispersion at 1° to 3° C. are added 178 parts of a 40% aqueous dimethylamine solution (1.58 moles). The compound No. 8 according to Table I is obtained as a crystalline substance.

Elementary analysis: Calculated: C, 36.05%; N, 22.93%; S, 31.83%; H, 4.62%; O, 4.57%. Found: C, 36.0%; N, 23.5%; S, 32.0%; H, 4.7%; O, 3.8%.

EXAMPLE 9

The procedure is carried out as given in Example 8 except that 121 parts (0.6 mole) of 2-isopropylamino-4,6-dimercapto-s-triazine are introduced in place of 129.6 parts (0.6 mole) of 2-diethylamino-4,6-dimercapto-s-triazine. The compound No. 9 according to Table I is obtained as a crystalline substance.

Elementary analysis: Calculated: C, 33.21%; N, 23.85%; S, 33.83%; H, 5.02%; O, 4.09%. Found: C, 33.5%; N, 24.2%; S, 33.3%; H, 4.9%; O, 4.1%.

EXAMPLE 10

The procedure is carried out as given in Example 4 except that to the aqueous s-triazine-2,4,6-trisulphochloride dispersion at 1° to 3° C. are added 125 parts of a 25% aqueous ammonia solution (1.84 moles) in place of 208 parts of the 40% aqueous dimethylamine solution (1.84 moles). The compound No. 10 according to Table I is obtained as a crystalline substance.

Elementary analysis: Calculated: C, 11.32%; N, 26.41%; S, 30.22%; H, 1.90%; O, 30.15%. Found: C, 10.9%; N, 26.9%; S, 29.8%; H, 2.0%; O, 30.4%.

EXAMPLE 11

The process is carried out as given in Example 4 except that to the aqueous s-triazine-2,4,6-trisulphochloride dispersion at 1° to 3° C. are added 143 parts of a 40% aqueous methylamine solution (1.84 moles) instead of 208 parts of the 40% aqueous dimethylamine solution (1.84 moles). The compound No. 11 according to Table I is obtained as a crystalline substance.

Elementary analysis: Calculated: C, 20.00%; N, 23.32%; S, 26.69%; H, 3.35%; O, 26.64%. Found: C, 20.2%; N, 23.0%; S, 26.3%; H, 3.5%; O, 27.0%.

EXAMPLE 12

36 parts (0.2 mole) of 2-methoxy-4,6-dichloro-s-triazine, dissolved in 400 parts of acetone, and 47.2 parts (0.4 mole) of the compound of the formula (13) are reacted with each other at the reflux temperature of 55° to 58° C. The still hot reaction mixture is freed by filtration from the sodium chloride and concentrated by evaporation. The product obtained is dispersed in water and the dispersion is rendered alkaline with an aqueous sodium hydroxide solution. As a result of this, the unreacted amount of the compound of the formula (13) goes into solution. The aqueous dispersion is filtered under suction and the residue is subsequently washed with water at 1° to 3° C. The compound No. 12 according to Table I is thus obtained in the form of a light-brown pulverulent substance.

Elementary analysis: Calculated: C, 16.05%; N, 32.76%; S, 21.43%; H, 3.03%; O, 26.73%. Found: C, 16.4%; N, 32.5%; S, 21.1%; H, 3.4%; O, 26.6%.

EXAMPLE 13

The procedure is carried out as given in Example 12 except that the 36 parts (0.2 mole) of 2-methoxy-4,6-dichloro-s-triazine are replaced by 48.4 parts (0.2 mole) of 2-phenoxy-4,6-dichloro-s-triazine. The compound No. 13 according to Table I is obtained as a pulverulent substance.

Elementary analysis: Calculated: C, 29.91%; N, 27.13%; S, 17.75%; H, 3.07%; O, 22.64%. Found: C, 29.7%; N, 26.8%; S, 17.3%; H, 2.9%; O, 23.3%.

EXAMPLE 14

The procedure is carried out as given in Example 12 except that 36 parts (0.2 mole) of 2-methoxy-4,6-dichloro-s-triazine are replaced by 51.2 parts (0.2 mole) of 2-benzyloxy-4,6-dichloro-s-triazine. The compound No. 14 according to Table I is obtained as a pulverulent substance.

Elementary analysis: Calculated: C, 32.00%; N, 26.12%; S, 17.08%; H, 3.49%; O, 21.31%. Found: C, 32.5%; N, 25.8%; S, 16.7%; H, 3.8%; O, 21.2%.

EXAMPLE 15

The procedure is carried out as given in Example 1 except that 18 parts (0.1 mole) of 2-methoxy-4,6-dichloro-s-triazine are replaced by 24.2 parts (0.1 mole) of 2-phenoxy-4,6-dichloro-s-triazine. The compound No. 15 according to Table I is obtained as a crystalline substance.

Elementary analysis: Calculated: C, 51.58%; N, 13.08%; S, 11.98%; H, 2.44%; O, 20.92%. Found: C, 51.2%; N, 12.7%; S, 11.5%; H, 2.1%; O, 22.5%.

EXAMPLE 16

The procedure is carried out as given in Example 1 except that 18 parts (0.1 mole) of 2-methoxy-4,6-dichloro-s-triazine are replaced by 25.6 parts (0.1 mole) of 2-benzyloxy-4,6-dichloro-s-triazine. The compound No. 16 according to Table I is obtained as a crystalline substance.

Elementary analysis: Calculated: C, 52.45%; N, 12.75%; S, 11.67%; H, 2.75%; O, 20.38%. Found: C, 51.9%; N, 12.4%; S, 11.2%; H, 2.9%; O, 21.6%.

EXAMPLE 17

Instruction for producing dispersions 200 g of s-triazine of the formula I is suspended in a solution of 4 g of the sodium salt of a condensation product from naphthalenesulphonic acid and formaldehyde, and 2 g of carboxymethylcellulose in 194 g of water. The suspension is ground in a sand mill until the mean particle diameter is $5\mu$. A readily pourable and dilutable dispersion is obtained.

APPLICATION EXAMPLE 18

Polyester fabrics having a weight per unit area of 150 g/m$^2$ are padded with the aqueous liquors according to the following Table II, dried for 30 minutes at about 80° C., and subsequently subjected to a thermosol treatment for 20 seconds at 200° C.

The fabric is then washed for 5 minutes at 60° C. in a liquor containing per liter 2 g of anhydrous sodium carbonate and 1 g of a condensation product from 1 mole of p-nonylphenol and 9 moles of ethylene oxide. The material is subsequently rinsed and dried.

The fixation degree indicates the amount of product present on the fiber material after the subsequent washing treatment (relative to the amount present after the thermosol treatment).

The fabrics are afterwards washed for 45 minutes at 60° C., in a domestic washing machine, in a liquor containing per liter 4 g of a household detergent (SNV 198 861—washing).

The individual fabric specimens are then tested with respect to their fireproofness (DIN 53 906, ignition times 3 seconds).

The results are given in the following Table II.

TABLE II

|  |  | un-treated | Treated with liquor | | | | | | | | |
|---|---|---|---|---|---|---|---|---|---|---|---|
|  |  |  | A* | B | C | D** | E | F | G | H | I |
| product | 1 |  | 100 |  |  |  |  |  |  |  |  |
| according to Example | 2 |  |  | 27 |  |  |  |  |  |  |  |
| (% in dispersion) | 3 |  |  |  |  |  |  |  |  |  | 100 |
|  | 4 |  |  |  | 21 |  |  |  |  |  |  |
|  | 5 |  |  |  |  | 100 |  |  |  |  |  |
|  | 6 |  |  |  |  |  | 16 |  |  |  |  |
|  | 7 |  |  |  |  |  |  | 20 |  |  |  |
|  | 8 |  |  |  |  |  |  |  | 33 |  |  |
|  | 9 |  |  |  |  |  |  |  |  | 18 |  |
| liquor absorption |  |  | 80 | 80 | 85 | 80 | 85 | 85 | 80 | 80 | 80 |
| g of dispersion/kg of licquor |  |  | 187 | 346 | 419 | 88 | 549 | 878 | 284 | 526 | 88 |
| handle after subsequent washing |  | 0 | 1 | 0 | ½ | ½ | ½ | 0 | 1 | 0 | 1 |
| flameproofness |  |  |  |  |  |  |  |  |  |  |  |
| after subsequent washing |  |  |  |  |  |  |  |  |  |  |  |
| burning time sec. |  |  | 1 | 2 | 2 | 2 | 6 | 6 | 7 | 1 | 0 |
| tear length cm. |  |  | 4.5 | 5 | 5.5 | 6.5 | 6.5 | 8 | 5 | 5 | 5.5 |
| after 20 machine washing |  | burns |  |  |  |  |  |  |  |  |  |
| burning time sec. |  |  | 0 | 0 | 8 | 0 | 10 | 9 | 10 | 4 | 0 |
| tear length cm. |  |  | 4 | 4.5 | 7.5 | 6 | 6 | 7.5 | 5 | 5 | 5 |
| after 40 machine washings |  |  |  |  |  |  |  |  |  |  |  |
| burning time sec. |  |  | 0 | 4 | 2 | 0 | 12 | 11 | 12 | 8 | 0 |
| tear length cm. |  |  | 4.5 | 5.5 | 6 | 6 | 7 | 6.5 | 7 | 6.5 | 5 |

Polyester fabrics dyed blue are finished with the liquors A, B, E, F, G and H.
Undyed but optically brightened polyester fabrics are finished with the liquors C, D and I.
Handle values:
0 unchanged
1 fraction stiffer than 0,
2 somewhat stiffer than 0,
3 stiff,
4 very stiff.
*in the case of this liquor it is a solution in dimethylformamide and not a dispersion; the % content of the dispersion is therefore given as 100
**here the product No. 3 or 6 has been added as it is, i.e. not as dispersion, to the liquor Similar results are obtained with the products according to Examples 10 to 16.

We claim:

1. s-Triazine of the formula

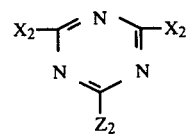

wherein $X_2$ is a radical of the formula $$-(NH)_{n-1}-SO_2-N\begin{matrix}R_7\\R_8\end{matrix} \quad (3.1)$$

wherein n is 1 or 2, and $R_7$ and $R_8$ each are phenyl, benzyl, alkyl with 1 to 4 carbon atoms, or hydrogen, and $Z_2$ has the meanings given for $X_2$, or is diethylamino or dimethylamino, and, if n in formula (3.1) is 2, $Z_2$ also is ethoxy, methoxy, phenoxy or benzyloxy.

2. s-Triazine of the formula

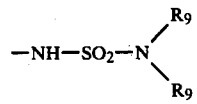

wherein $X_3$ is a radical of the formula $$-NH-SO_2-N\begin{matrix}R_9\\R_9\end{matrix} \quad (4.1)$$

wherein $R_9$ is methyl or hydrogen, and $Z_3$ has the meanings given for $X_3$ or is methoxy, phenoxy or benzyloxy.

* * * * *